US012672888B2

(12) United States Patent
Patriciu

(10) Patent No.: US 12,672,888 B2
(45) Date of Patent: Jul. 7, 2026

(54) SYSTEMS AND METHODS FOR CLOT RETRIEVAL IN MECHANICAL THROMBECTOMY

(71) Applicant: KONINKLIJKE PHILIPS N.V., Eindhoven (NL)

(72) Inventor: Alexandru Patriciu, Belmont, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 221 days.

(21) Appl. No.: 18/560,765

(22) PCT Filed: May 13, 2022

(86) PCT No.: PCT/EP2022/063003
§ 371 (c)(1),
(2) Date: Nov. 14, 2023

(87) PCT Pub. No.: WO2022/243181
PCT Pub. Date: Nov. 24, 2022

(65) Prior Publication Data
US 2024/0252188 A1 Aug. 1, 2024

Related U.S. Application Data

(60) Provisional application No. 63/189,751, filed on May 18, 2021.

(51) Int. Cl.
*A61B 17/22* (2006.01)
*A61B 17/00* (2006.01)
(Continued)

(52) U.S. Cl.
CPC ............. *A61B 17/22* (2013.01); *A61B 34/32* (2016.02); *G06T 7/0012* (2013.01); *G06T 7/60* (2013.01);
(Continued)

(58) Field of Classification Search
CPC .................. A61B 17/22; A61B 17/221; A61B 2017/00119; A61B 2017/22034;
(Continued)

(56) References Cited

U.S. PATENT DOCUMENTS

| | | |
|---|---|---|
| 2019/0374128 A1 | 12/2019 | Palushi |
| 2020/0253670 A1 | 8/2020 | Doisneau |
| 2021/0145466 A1 | 5/2021 | Friedman |

FOREIGN PATENT DOCUMENTS

| | | |
|---|---|---|
| WO | 2020/099386 A1 | 5/2020 |
| WO | 2021055428 A1 | 3/2021 |

OTHER PUBLICATIONS

International Search Report and Written Opinion Dated Aug. 25, 2022 For International Application No. PCT/EP2022/063003 Filed May 13, 2022.
(Continued)

*Primary Examiner* — Amelie R Davis

(57) ABSTRACT

A vascular therapy device (10) includes a retrieval device (12) configured to deploy an associated self-expanding stent (2) in a clot and including a retrieval line (14) attached to the associated self-expanding stent. At least one electronic processor (20) is programmed to: receive a time sequence of images (35) of the associated self-expanding stent acquired during a thrombectomy procedure in which the self-expanding stent is deployed in a clot; perform image analysis on the images of the time sequence of images to determine a geometric change of the associated self-expanding stent deployed in the clot; identify an event occurring in the thrombectomy procedure based on the geometric change of the associated self-expanding stent deployed in the clot; and respond to the identification of the event by: outputting an indication (36) of the event; and/or controlling a robot (16) to perform an action in response to the event.

20 Claims, 3 Drawing Sheets

(51) Int. Cl.

| | |
|---|---|
| *A61B 34/32* | (2016.01) |
| *A61B 90/00* | (2016.01) |
| *G06T 7/00* | (2017.01) |
| *G06T 7/60* | (2017.01) |

(52) U.S. Cl.
CPC ............... *A61B 2017/00119* (2013.01); *A61B 2017/22094* (2013.01); *A61B 2090/376* (2016.02); *G06T 2207/10116* (2013.01); *G06T 2207/30101* (2013.01); *G06T 2207/30204* (2013.01)

(58) Field of Classification Search
CPC .. A61B 2017/22094; A61B 2034/2065; A61B 2034/301; A61B 2090/374; A61B 2090/376; A61B 2090/3762; A61B 2090/3966; A61B 34/30; A61B 90/37; G06T 2207/10116; G06T 2207/30101; G06T 2207/30204; G06T 7/0012; G06T 7/60
See application file for complete search history.

(56) References Cited

OTHER PUBLICATIONS

Autar, et al: "High-Resolution Imaging of Interaction Between Thrombus and Stent-Retriever in Patients With Acute Ischemic Stroke", Jun. 2021.

initial deployment     Fig. 3a stent retriever integrated in the clot     Fig. 3b Stent force = sum of friction forces Friction force
Clot-blood vessel walls
clot extraction

FIG. 3a-c

SYSTEMS AND METHODS FOR CLOT RETRIEVAL IN MECHANICAL THROMBECTOMY

CROSS REFERENCE TO RELATED APPLICATIONS

This application is the U.S. National Phase application under 35 U.S.C. § 371 of International Application No. PCT/EP2022/063003 filed May 13, 2022, which claims the benefit of U.S. Provisional Patent Application No. 63/189, 751 filed May 18, 2021. These applications are hereby incorporated by reference herein.

FIELD

The following relates generally to the catheter arts, thrombectomy arts, imaging arts, clot retrieval arts, and related arts.

BACKGROUND

Vascular therapy (e.g., thrombectomy, atherectomy, and so forth) devices are medical devices designed to remove or modify tissue or material from inside a diseased vessel (e.g., an artery, a vein, etc.). In particular, mechanical thrombectomy is an effective treatment for ischemic strokes by direct removal of arterial brain clots. In such procedures, a removal device is deployed through the clot. Proper device selection and placement is important for procedure success. Typically, a stent retriever can be used for such procedures.

A mechanical thrombectomy typically includes the following steps: (1) access a thrombus or clot site using a micro-catheter/micro-guidewire combination; (2) advance the micro-guidewire past the thrombus; (3) advance the micro-catheter over the micro-guidewire past the thrombus; (4) retract the micro-guidewire and replace with stent retriever; (5) deploy the stent retriever; and (6) wait for stent integration with the clot; and (7) retrieve the thrombus by retracting together the stent retriever and microcatheter into the balloon guide catheter while applying suction on the catheter.

However, in step (7), the stent-retriever retraction should be such that the clot is retrieved in one piece, and with a single attempt, to reduce ischemia that causes permanent brain tissue damage. If, during retrieval, there are fragments of the clot that detach these will lodge into and obstruct smaller arteries downstream. These can be difficult or impossible to retrieve, potentially leading to complications.

The following discloses certain improvements to overcome these problems and others.

SUMMARY

In some embodiments disclosed herein, a vascular therapy device includes a retrieval device configured to deploy an associated self-expanding stent in a clot and including a retrieval line attached to the associated self-expanding stent. At least one electronic processor is programmed to: receive a time sequence of images of the associated self-expanding stent acquired during a thrombectomy procedure in which the self-expanding stent is deployed in a clot; perform image analysis on the images of the time sequence of images to determine a geometric change of the associated self-expanding stent deployed in the clot; identify an event occurring in the thrombectomy procedure based on the geometric change of the associated self-expanding stent deployed in the clot;

and respond to the identification of the event by: outputting an indication of the event; and/or controlling a robot to perform an action in response to the event.

In some embodiments disclosed herein, a vascular therapy apparatus includes a self-expanding stent including one or more radiopaque markers. A retrieval device is configured to deploy the self-expanding stent in a clot and including a retrieval line attached to the self-expanding stent. At least one electronic processor is programmed to: receive a time sequence of images of the self-expanding stent acquired during a thrombectomy procedure in which the self-expanding stent is deployed in a clot; perform image analysis on the images of the time sequence of images to determine a geometric change of the self-expanding stent deployed in the clot based on a change in configuration of the one or more radiopaque markers in successive images of the time sequence of images of the self-expanding stent acquired during the thrombectomy procedure; identify an event occurring in the thrombectomy procedure based on the geometric change of the self-expanding stent deployed in the clot; and respond to the identification of the event by: outputting an indication of the event; and/or controlling a robot to perform an action in response to the event.

In some embodiments disclosed herein, a vascular therapy device includes a retrieval device configured to deploy an associated self-expanding stent in a clot and including a retrieval line attached to the associated self-expanding stent. A stent retrieval robot is operatively connected to the retrieval line and configured to control retrieval of the associated self-expanding stent deployed in the clot via the retrieval line. An X-ray imaging device is configured to acquire a time sequence of images of the associated self-expanding stent acquired during a thrombectomy procedure. At least one electronic processor is programmed to: receive the time sequence of images of the associated self-expanding stent acquired during the thrombectomy procedure in which the self-expanding stent is deployed in a clot; perform image analysis on the images of the time sequence of images to determine a geometric change of the associated self-expanding stent deployed in the clot; identify an event occurring in the thrombectomy procedure based on the geometric change of the associated self-expanding stent deployed in the clot; and respond to the identification of the event by: outputting an indication of the event; and/or controlling the stent retrieval robot to perform an action in response to the event.

One advantage resides in providing a stent retrieval device that allows the stent to withdraw a clot in a single attempt.

Another advantage resides in providing improved control of a stent retrieval process to reduce likelihood of a clot breaking into smaller fragments.

Another advantage resides in providing mechanical thrombectomy with improved timing of the stent retrieval to ensure full integration with the clot while avoiding unnecessary delay in initiating the stent retrieval.

Another advantage resides in providing feedback during stent retrieval to determine a geometric change in the stent.

Another advantage resides in controlling a speed of a robotic member withdrawing a stent integrated with a clot in a patient.

A given embodiment may provide none, one, two, more, or all of the foregoing advantages, and/or may provide other advantages as will become apparent to one of ordinary skill in the art upon reading and understanding the present disclosure.

3

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

FIGS. 3A-C diagrammatically illustrate other views of the device of FIG. 1.

DETAILED DESCRIPTION

The following relates to mechanical thrombectomy, which is a technique in which a self-expanding (e.g., nitinol) stent that is tied to a retrieval line is deployed into a clot. The stent expands and integrates with the clot, and then the stent with the integrated clot is pulled back into the catheter using the retrieval line to remove the clot from the bloodstream.

In this procedure, it is important for the stent to integrate with the clot to the greatest extent achievable, to ensure the clot is retrieved along with the stent. Furthermore, the speed at which the stent is retrieved is important—if the stent is drawn back too quickly this can result in increased friction between the blood vessel wall and the clot causing a portion of the clot to dislodge from the stent.

Presently, the deployed stent is left in the clot for a fixed time interval expected to be sufficient for full integration with the clot. However, this is not always the case. Furthermore, presently the stent retrieval process is not monitored beyond monitoring the retrieval speed.

The following discloses using fluoroscope (or other) imaging to decide the integration time, and to use the fluoroscope imaging to monitor the stent retrieval process.

The disclosed approaches for deciding the integration time are based on the following insight. The self-expanding stent is expected to continue expanding until it is maximally integrated with the clot, at which point the stent expansion stops. Stent expansion involves two dimensional changes: increase in stent diameter, and concomitant reduction in stent length as the stent expands. In embodiments disclosed herein, these dimensions are monitored by the fluoroscope imaging using radiopaque markers or coatings on the stent. In a manual embodiment, a light or audio signal indicates to the operator when full integration is achieved based on when the stent expansion has ceased.

In another aspect, the fluoroscopic or other imaging is used to monitor the stent retrieval process to avoid incomplete retrieval. Monitoring of the stent retrieval is based on the insight that as the stent begins to lose integration with the clot, the stent geometry is likely to initially partially collapse as the clot begins to move relative to the stent. This geometric change can again be observed by the fluoroscopy, and a warning light or warning alarm triggered by a detected significant change in stent geometry. The warning may, for example, indicate to the operator that the stent retrieval speed should be reduced.

In a robotic embodiment, the above-described inputs can be used to automatically trigger initiation of the stent retrieval once stent expansion has stopped and to automatically slow the retrieval speed if stent geometry begins to change during retrieval.

Figure 1:
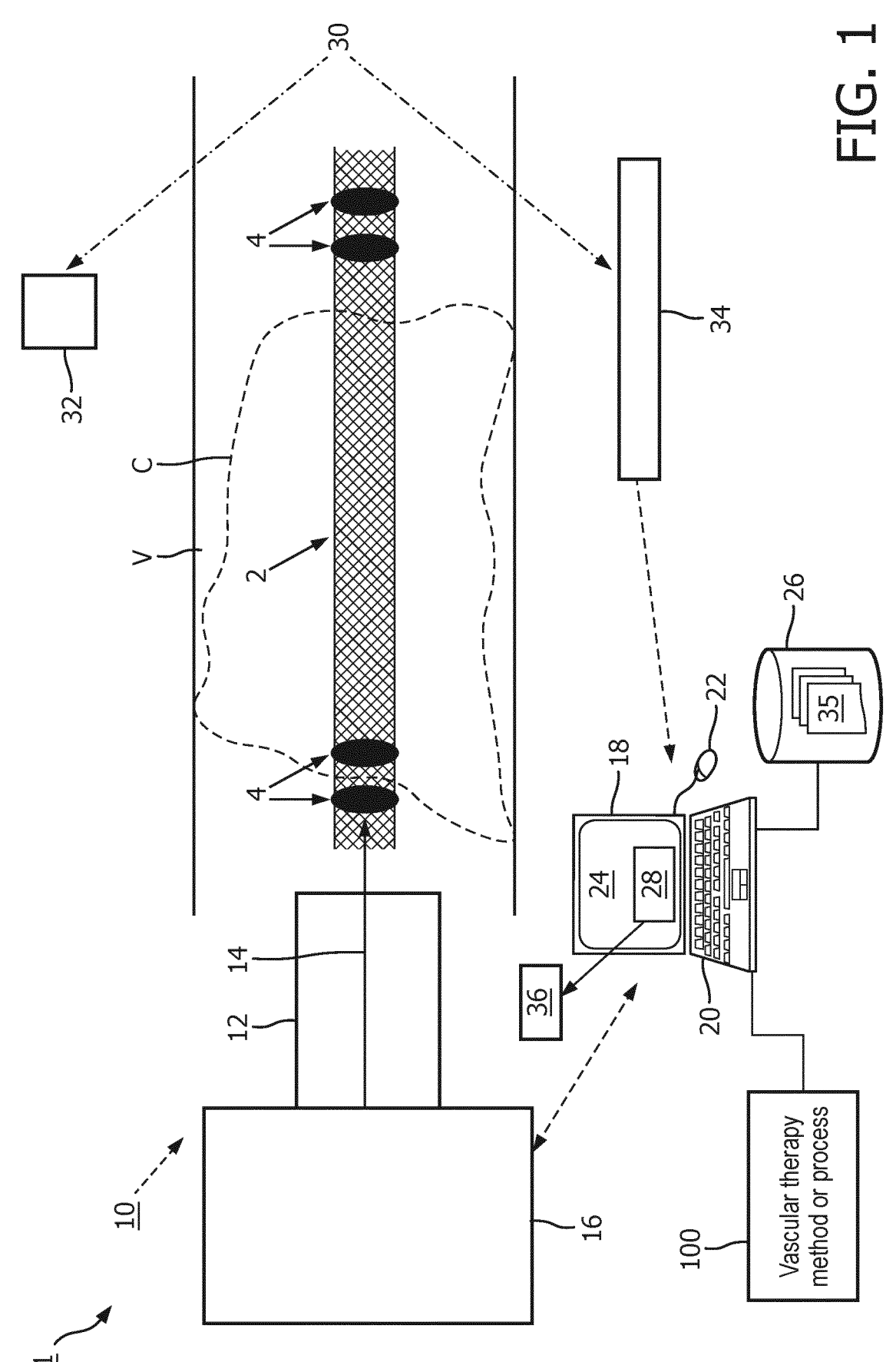
FIG. 1 diagrammatically illustrates a vascular therapy device in accordance with the present disclosure.

With reference to FIG. 1, an illustrative vascular therapy (i.e., thrombectomy or atherectomy) apparatus 1 is diagrammatically shown. As shown in FIG. 1, the apparatus 1 includes a therapy device 10 for delivering and retrieving a self-expanding vascular therapy device 2 (e.g., a self-expanding stent, a self-expanding filter, and so forth) into a blood vessel. The therapy device 10 includes a retrieval device 12 configured to deploy the self-expanding stent 2 in a clot C (diagrammatically shown in FIG. 1 with dashed lines) in a blood vessel V of a patient. The retrieval device 12 includes a retrieval line 14 attached to the self-expanding stent 2. As shown in FIG. 1, the self-expanding stent 2 can include one or more radiopaque markers 4 (three of which are shown in FIG. 1, although any suitable number of markers can be used). The radiopaque markers 4 can take any form, such as a radiopaque coating applied to some portion or all of the wires or other material making up the stent 2, and/or separate radiopaque marker elements attached to the stent by metallurgical bonds, or so forth.

FIG. 1 also shows a stent retrieval robot 16 (diagrammatically shown in FIG. 1 as a box) operatively connected to the retrieval line 14. The robot 16 is configured to control retrieval of the self-expanding stent 2 deployed in the clot C via the retrieval line 14. FIG. 1 further shows an electronic processing device 18, such as a workstation computer, or more generally a computer. The electronic processing device 18 may also include a server computer or a plurality of server computers, e.g., interconnected to form a server cluster, cloud computing resource, or so forth, to perform more complex computational tasks. The workstation 18 includes typical components, such as an electronic processor 20 (e.g., a microprocessor), at least one user input device (e.g., a mouse, a keyboard, a trackball, and/or the like) 22, and a display device 24 (e.g., an LCD display, plasma display, cathode ray tube display, and/or so forth). In some embodiments, the display device 24 can be a separate component from the workstation 18 or may include two or more display devices.

The electronic processor 20 is operatively connected with one or more non-transitory storage media 26. The non-transitory storage media 26 may, by way of non-limiting illustrative example, include one or more of a magnetic disk, RAID, or other magnetic storage medium; a solid-state drive, flash drive, electronically erasable read-only memory (EEROM) or other electronic memory; an optical disk or other optical storage; various combinations thereof; or so forth; and may be for example a network storage, an internal hard drive of the workstation 18, various combinations thereof, or so forth. It is to be understood that any reference to a non-transitory medium or media 26 herein is to be broadly construed as encompassing a single medium or multiple media of the same or different types. Likewise, the electronic processor 20 may be embodied as a single electronic processor or as two or more electronic processors. The non-transitory storage media 26 stores instructions executable by the at least one electronic processor 20. The instructions include instructions to generate a visualization of a graphical user interface (GUI) 28 for display on the display device 24.

In a manual embodiment, the stent retrieval robot 16 is suitably replaced by a manual mechanism for performing the stent retrieval. In this embodiment, the GUI 28 suitably presents an alert when (as described below) the stent retrieval should begin, and/or an alarm if (as described below) the stent is detected to be losing integration with the clot during the manually performed stent retrieval.

FIG. 1 also shows an imaging device 30 configured to acquire images 35 of the self-expanding stent 2 during a thrombectomy procedure. In particular, in the illustrative examples the imaging device 30 is a fluoroscopic imaging device (e.g., an X-ray imaging device, C-arm imaging device, a CT scanner, or so forth) and the radiopaque markers 4 attached to the self-expanding stent 2 are visible under imaging, thereby allowing a position of the self-expanding stent 2 relative to the clot C to be determined. The imaging device 30 is in communication with the at least one electronic processor 20 of the electronic processing device 18. As shown in FIG. 1, the imaging device 30 comprises an X-ray imaging device including an X-ray source 32 and an X-ray detector 34, such as a C-arm imaging device; however, it will be appreciated that any suitable imaging device, such as ultrasound (US), computed tomography (CT), magnetic resonance imaging (MRI), nuclear imaging, or any other suitable imaging device may be used. For non-fluoroscopic imaging devices, the radiopaque markers 4 are suitably replaced by markers of a type that is observable in the chosen imaging modality. For example, if MRI is used for monitoring, then the markers 4 are suitably markers that provide good contrast in MRI images. The images 35 can be stored in the non-transitory storage media 26.

The at least one electronic processor 20 is configured as described above to perform a vascular therapy method or process 100. The non-transitory storage medium 26 stores instructions which are readable and executable by the at least one electronic processor 20 to perform disclosed operations including performing the vascular therapy method or process 100. In some examples, the method 100 may be performed at least in part by cloud processing.

Figure 2:
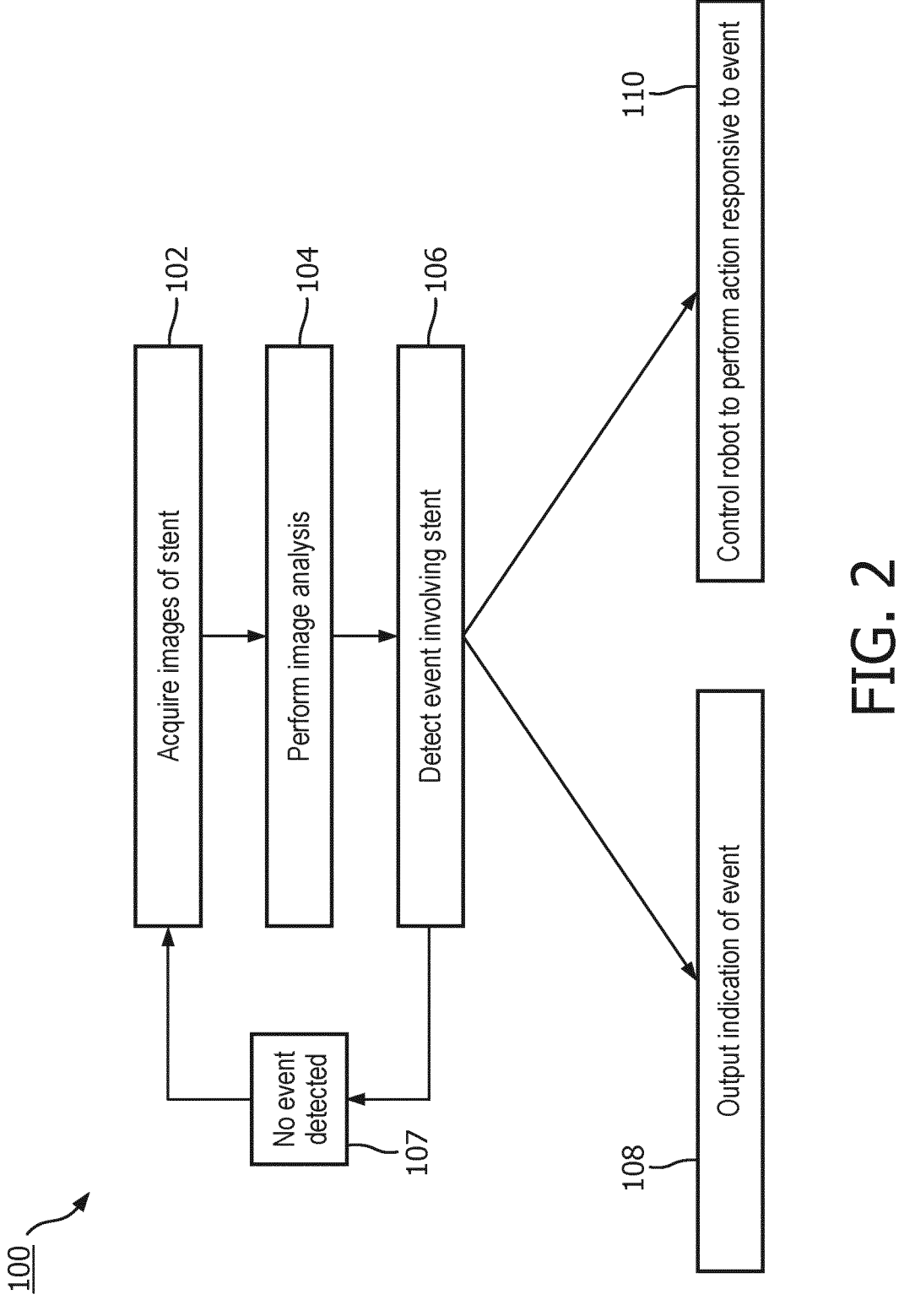
FIG. 2 diagrammatically illustrates a method of performing a vascular therapy method using the device of FIG. 1.

Referring to FIG. 2, and with continuing reference to FIG. 1, an illustrative embodiment of the vascular therapy method 100 is diagrammatically shown as a flowchart. To begin the method 100, the self-expanding stent 2 is deployed into the blood vessel V via the therapy device 10 into the clot C. At an operation 102, the imaging device 30 acquires a time sequence of images of the self-expanding stent 2 acquired during a thrombectomy procedure in which the self-expanding stent 2 is deployed in a clot C. The time sequence of images is then transferred to the electronic processing device 18.

At an operation 104, image analysis is performed on the images of the time sequence of images to determine a geometric change of the self-expanding stent 2 deployed in the clot C. In some embodiments, the image analysis is performed based on a change in configuration of one or more of the radiopaque markers 4 in successive images of the time sequence of images of the self-expanding stent 2 acquired during the thrombectomy procedure at the operation 102.

At an operation 106, if an event is identified the thrombectomy procedure based on the geometric change of the self-expanding stent 2, then a response is performed based on the identification of the event at the operation 106; otherwise, flow passes 107 back in iterative fashion to operation 102 to continue acquiring images until an iteration of the operation 106 identifies an event. In some embodiments, at an operation 108, the response includes outputting an indication 36 of the event. To do so, the indication 36 can be a visual message or warning displayed on the display device 24, an audible indication output by the electronic processing device 18, and so forth.

In one example, the event is identified prior to retrieval of the self-expanding stent 2. The event comprises a cessation of expansion of the self-expanding stent 2 while deployed in the clot C. Responsive to this identification, the indication 36 is output and indicates that stent retrieval should be initiated.

In another example, the event is identified during retrieval of the self-expanding stent 2. The event comprises a detection of partial collapse of the self-expanding stent 2. Responsive to this identification, the indication 36 is output and comprises a warning that the stent retrieval rate should be reduced (e.g., by controlling a speed at which the robot 16 withdraws the retrieval device 12).

In some embodiments, at an operation 110, the response includes controlling the robot 16 to perform an action in response to the event (e.g., withdraw the self-expanding stent 2 via the retrieval device 12, slow a speed of withdrawal of the self-expanding stent 2, and so forth).

In one example, the event is identified prior to retrieval of the self-expanding stent 2 from the clot C. The event comprises a cessation of expansion of the self-expanding stent 2 deployed in the clot C. Responsive to this identification, the robot 16 is controlled to initiate the retrieval of the self-expanding stent 2 in response to the cessation of the expansion of the self-expanding stent 2 deployed in the clot C.

In another example, the event is identified during retrieval of the self-expanding stent 2 deployed in the clot. The event comprises a detection of partial collapse of the self-expanding stent 2. Responsive to this identification, the robot 16 is controlled to reduce a rate of the retrieval of the self-expanding stent 2 deployed in the clot C in response to the partial collapse of the self-expanding stent 2.

In other embodiments, both operations 108 and 110 can be performed. For example, once an indication 36 is output at the operation 108, the robot 16 can be controlled to retrieve the self-expanding stent 2 at the operation 110.

EXAMPLE

With continuing references to FIGS. 1 and 2, FIGS. 3A-C show example operations of the apparatus 1 in more detail. The apparatus 1 is implemented for two objectives—(1) ensure that the self-expanding stent 2 integrates fully with the clot C, and (2) ensure that the clot C is fully extracted with the retrieval device 12.

To do so, the retrieval device 12 is detected in images acquired by the imaging device 30. In particular, the markers 4 on the self-expanding stent 2 are identifiable in the images to determine the position of the retrieval device 12. Image filters can then be employed to detect individual wires of the self-expanding stent 2. When these wires are detected, an estimate of the main characteristics of the shape of the self-expanding stent 2 can be obtained.

During deployment of the self-expanding stent 2, X-ray images 35 are acquired of the self-expanding stent 2, which are (at least temporarily) stored in the non-transitory computer readable medium 26 of the electronic processing device 18. FIG. 3A shows the retrieval device 12 immediately after deployment of the self-expanding stent 2 in the clot C. As time elapses, the self-expanding stent 2 opens until it reaches a stable expanded state. The electronic processing device 18 monitors the shape of the self-expanding stent 2 via image processing of the images 35 by comparing the shapes in consecutive images. If the shapes are determined to be the same, then stent integration with clot C is deemed to be complete (as shown in FIG. 3B), and the self-expanding stent 2 can be extracted. The shape of the self-expanding stent 2 can be thoroughly characterized by detecting each wire of the self-expanding stent 2 or by using synthetic values such as stent length and width of the self-expanding stent 2 deployed inside the clot C.

Figure 3C:
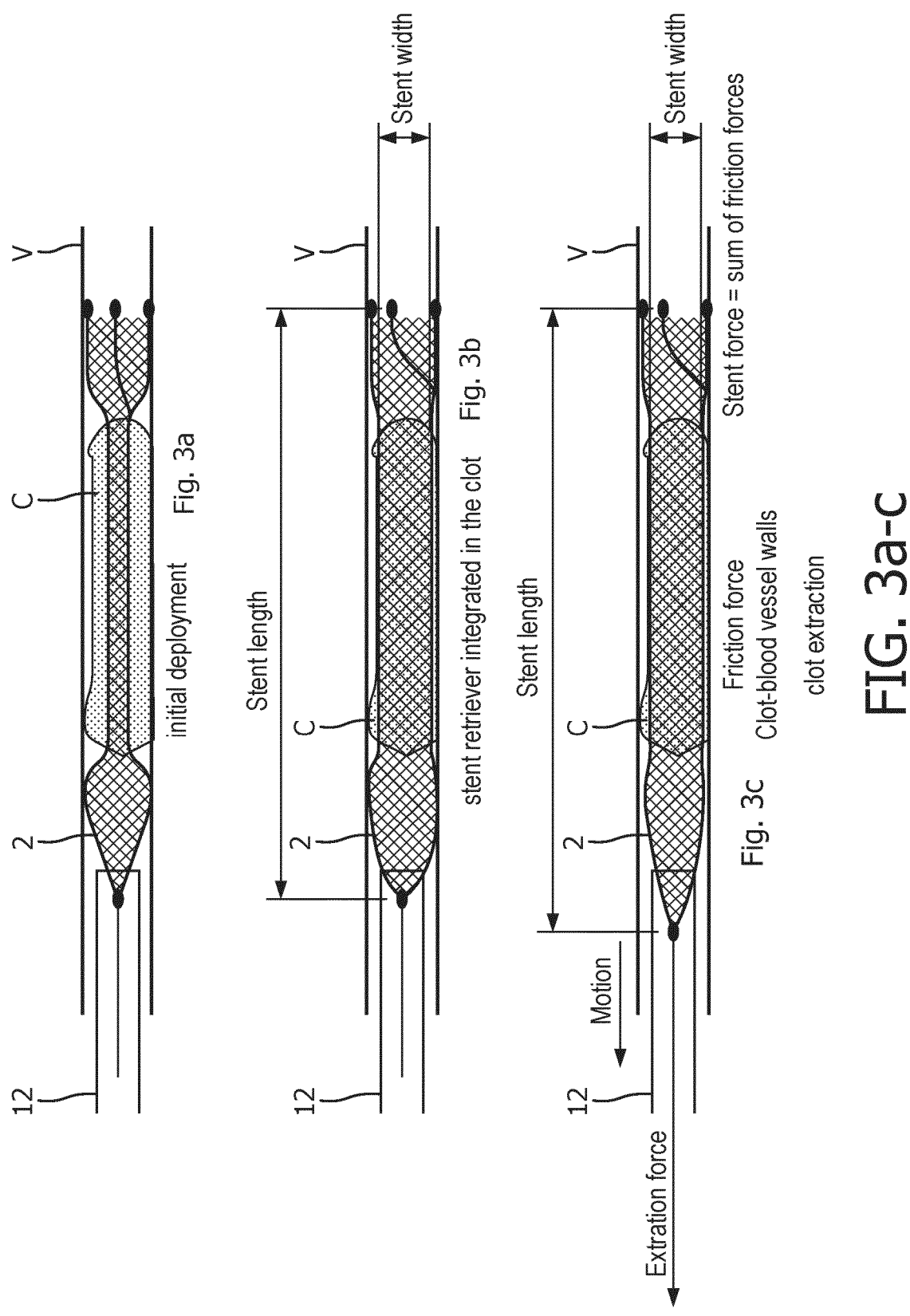

FIG. 3C shows forces that act on the clot C and the retrieval device 12 due to the clot extraction process. There are two opposing forces: (1) an extraction force applied on the retrieval line 14 and transmitted by the self-expanding stent 2 to the clot C, and (2) a distributed friction force between the clot C and walls of the blood vessel V. The retrieval device 12 distributes the extraction force throughout the clot volume, thereby allowing the cancelation of the friction without force concentrations. This allows for the removal of the entire clot C ideally without fragmentation. The self-expanding stent 2 should stay open during the extraction process. The friction force has several components: a static component that will be minimal once the stent starts moving and a viscous friction that is proportional with the velocity of extraction. If these forces are large, then the stent will collapse, and the clot extraction will fail. By controlling the extraction speed, the viscous friction force can be controlled.

During the extraction, the shape of the self-expanding stent 2 can change. To control the extraction process, the shape of the self-expanding stent 2 at an end of the clot C (e.g., $S_0$) is stored in the non-transitory computer readable medium 26. The extraction is then started with an initial velocity $v_0$. The images 35 are then acquired. For each image 35, the image is processed to extract a shape $S_c$ of the self-expanding stent 2 and compared to the initial shape $S_0$. If the shape $S_c$ is determined to be collapsing, then the velocity of the stent extraction is reduced. If the shape $S_c$ is determined to be stable, then the velocity of the stent extraction is increased to minimize extraction time. In one specific embodiment, the following steps are employed to control the stent extraction:

(1) Store the stent shape ($S_0$) at the end of the clot-stent integration stage.

(2) Start the extraction with initial velocity $v=v_0$.

(3) Acquire X-ray images. For each X-ray image (a) Process the image and extract the stent shape $S_C$ (b) Compare $S_C$ with $S_0$;

(i) If the stent is collapsing reduce the extraction velocity v.

(ii) If the stent is stable the extraction velocity can be increased to minimize the extraction time.

In a manual embodiment, these techniques can be implemented using the endo-vascular robotic device 16 that controls the motion of the retrieval line 14 and the retrieval device 12, and/or with feedback provided to the user as a display of virtual models. For example, during extraction, a virtual model of the self-expanding stent 2 with shape $S_0$ is overlaid on current stent retriever position. A user can then easily compare the two shapes and adjust the extraction velocity accordingly. Furthermore, the manipulation of the retrieval line 14 and the retrieval device 12, can be purely manual, or it can be done using a device that moves the retrieval line 14 according to user inputs, in case of remote control. This operation can be used to provide additional feedback such as highlight stent areas are not engaging, or highlight the speed of engagement for different sections which could indicate the elasticity of the clot C.

These approaches can be used as well in other fields such as lead extraction and chronic total occlusion (CTO). The application is developed using X-ray images obtained from a C-arm like device. However, same concepts can be implemented using other imaging modalities such as CT, MRI, US, etc.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A vascular therapy device, comprising:

a retrieval device configured to deploy a self-expanding stent in a clot and including a retrieval line attached to the self-expanding stent; and at least one electronic processor programmed to:

receive a time sequence of images of the self-expanding stent acquired during a thrombectomy procedure in which the self-expanding stent is deployed in a clot;

perform image analysis on the images of the time sequence of images to determine a geometric change of the self-expanding stent deployed in the clot;

identify an event occurring in the thrombectomy procedure based on the geometric change of the self-expanding stent deployed in the clot; and respond to the identification of the event by:

outputting an indication of the event; and/or controlling a robot to perform an action in response to the event.

2. The vascular therapy device of claim 1, further comprising:

a stent retrieval robot operatively connected to the retrieval line, and configured to control retrieval of the self-expanding stent deployed in the clot via the retrieval line, wherein the at least one electronic processor is programmed to respond to the identification by controlling the stent retrieval robot to initiate or modify the retrieval in response to the event.

3. The vascular therapy device of claim 2, wherein the event is detected prior to retrieval of the self-expanding stent deployed in the clot; and the event comprises a cessation of expansion of the self-expanding stent deployed in the clot; and the at least one electronic processor is programmed to respond to the identification by controlling the stent retrieval robot to initiate the retrieval of the self-expanding stent deployed in the clot in response to the cessation of the expansion of the self-expanding stent deployed in the clot.

4. The vascular therapy device of claim 3, wherein the event is detected during retrieval of the self-expanding stent deployed in the clot; and the event comprises a detection of partial collapse of the self-expanding stent; and the at least one electronic processor is programmed to respond to the identification by controlling the stent retrieval robot to reduce a rate of the retrieval of the self-expanding stent deployed in the clot in response to the partial collapse of the self-expanding stent.

5. The vascular therapy device of claim 1, wherein the at least one electronic processor is programmed to respond to the identification by outputting the indication of the event.

6. The vascular therapy device of claim 1, wherein the event is detected prior to retrieval of the self-expanding stent deployed in the clot; and the event comprises a cessation of expansion of the self-expanding stent deployed in the clot; and the at least one electronic processor is programmed to respond to the identification by outputting an indication that stent retrieval should be initiated.

7. The vascular therapy device of claim 1, wherein the event is detected during retrieval of the self-expanding stent deployed in the clot; and the event comprises a detection of partial collapse of the self-expanding stent and;

the at least one electronic processor is programmed to respond to the identification by outputting a warning that the stent retrieval rate should be reduced.

8. The vascular therapy device of claim 1, further comprising:

an imaging device configured to acquire the time sequence of images of the self-expanding stent acquired during the thrombectomy procedure;

wherein the imaging device is in communication with the at least one electronic processor.

9. The vascular therapy device of claim 8, wherein the imaging device comprises an X-ray imaging device including an X-ray source and an X-ray detector.

10. The vascular therapy device of claim 1, wherein the self-expanding stent includes one or more radiopaque markers; and wherein the at least one electronic processor is programmed to perform the image analysis based on a change in configuration of the one or more radiopaque markers in successive images of the time sequence of images of the self-expanding stent acquired during the thrombectomy procedure.

11. A vascular therapy apparatus, comprising:

a self-expanding stent including one or more radiopaque markers;

a retrieval device configured to deploy the self-expanding stent in a clot and including a retrieval line attached to the self-expanding stent; and at least one electronic processor programmed to:

receive a time sequence of images of the self-expanding stent acquired during a thrombectomy procedure in which the self-expanding stent is deployed in a clot;

perform image analysis on the images of the time sequence of images to determine a geometric change of the self-expanding stent deployed in the clot based on a change in configuration of the one or more radiopaque markers in successive images of the time sequence of images of the self-expanding stent acquired during the thrombectomy procedure;

identify an event occurring in the thrombectomy procedure based on the geometric change of the self-expanding stent deployed in the clot; and respond to the identification of the event by:

outputting an indication of the event; and/or controlling a robot to perform an action in response to the event.

12. The vascular therapy apparatus of claim 11, further comprising:

a stent retrieval robot operatively connected to the retrieval line, and configured to control retrieval of the self-expanding stent deployed in the clot via the retrieval line, wherein the at least one electronic processor is programmed to respond to the identification by controlling the stent retrieval robot to initiate or modify the retrieval in response to the event.

13. The vascular therapy apparatus of claim 12, wherein the event is detected prior to retrieval of the self-expanding stent deployed in the clot; and the event comprises a cessation of expansion of the self-expanding stent deployed in the clot; and the at least one electronic processor is programmed to respond to the identification by controlling the stent retrieval robot to initiate the retrieval of the self-expanding stent deployed in the clot in response to the cessation of the expansion of the self-expanding stent deployed in the clot.

14. The vascular therapy apparatus of claim 13, wherein the event is detected during retrieval of the self-expanding stent deployed in the clot; and the event comprises a detection of partial collapse of the self-expanding stent; and the at least one electronic processor is programmed to respond to the identification by controlling the stent retrieval robot to reduce a rate of the retrieval of the self-expanding stent deployed in the clot in response to the partial collapse of the self-expanding stent.

15. The vascular therapy apparatus of claim 11, wherein the at least one electronic processor is programmed to respond to the identification by outputting the indication of the event.

16. The vascular therapy apparatus of claim 11, wherein the event is detected prior to retrieval of the self-expanding stent deployed in the clot; and the event comprises a cessation of expansion of the self-expanding stent deployed in the clot; and the at least one electronic processor is programmed to respond to the identification by outputting an indication that stent retrieval should be initiated.

17. The vascular therapy apparatus of claim 11, wherein the event is detected during retrieval of the self-expanding stent deployed in the clot; and the event comprises a detection of partial collapse of the self-expanding stent and;

the at least one electronic processor is programmed to respond to the identification by outputting a warning that the stent retrieval rate should be reduced.

18. The vascular therapy apparatus of claim 11, further comprising:

an X-ray imaging device configured to acquire the time sequence of images of the self-expanding stent acquired during the thrombectomy procedure;

wherein the imaging device is in communication with the at least one electronic processor.

19. A vascular therapy device, comprising:

a retrieval device configured to deploy a self-expanding stent in a clot and including a retrieval line attached to the self-expanding stent;

a stent retrieval robot operatively connected to the retrieval line, and configured to control retrieval of the self-expanding stent deployed in the clot via the retrieval line;

an X-ray imaging device configured to acquire a time sequence of images of the self-expanding stent acquired during a thrombectomy procedure in which the self-expanding stent is deployed in a clot; and at least one electronic processor programmed to:

receive the time sequence of images of the self-expanding stent acquired during the thrombectomy procedure;

perform image analysis on the images of the time sequence of images to determine a geometric change of the self-expanding stent deployed in the clot;

identify an event occurring in the thrombectomy procedure based on the geometric change of the self-expanding stent deployed in the clot; and respond to the identification of the event by:

outputting an indication of the event; and/or controlling the stent retrieval robot to perform an action in response to the event.

20. The vascular therapy device of claim 19, wherein said self-expanding stent includes one or more radiopaque markers; and wherein the at least one electronic processor is programmed to perform the image analysis based on a change in configuration of the one or more radiopaque markers in successive images of the time sequence of images of the self-expanding stent acquired during the thrombectomy procedure.

5

\* \* \* \* \*